(12) United States Patent
Paris et al.

(10) Patent No.: US 10,123,096 B2
(45) Date of Patent: *Nov. 6, 2018

(54) IMPLANT TELEMETRY WITH DYNAMIC TUNING

(71) Applicants: Jacques Paris, Los Angeles, CA (US); Didier Sagan, San Diego, CA (US)

(72) Inventors: Jacques Paris, Los Angeles, CA (US); Didier Sagan, San Diego, CA (US)

(73) Assignee: MINIPUMPS, LLC, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/293,762

(22) Filed: Oct. 14, 2016

(65) Prior Publication Data

US 2017/0034601 A1 Feb. 2, 2017

Related U.S. Application Data

(63) Continuation-in-part of application No. 14/818,510, filed on Aug. 5, 2015, now Pat. No. 9,489,549.

(60) Provisional application No. 62/033,557, filed on Aug. 5, 2014.

(51) Int. Cl.
*H04Q 9/00* (2006.01)
*A61M 5/142* (2006.01)
*G06Q 30/00* (2012.01)
*H04B 5/00* (2006.01)

(52) U.S. Cl.
CPC .......... *H04Q 9/00* (2013.01); *A61M 5/14276* (2013.01); *G06Q 30/00* (2013.01); *H04B 5/00* (2013.01); *A61M 2205/3523* (2013.01); *A61M 2205/8206* (2013.01); *A61M 2205/8243* (2013.01); *H04B 5/0037* (2013.01); *H04B 5/0075* (2013.01); *H04Q 2209/40* (2013.01)

(58) Field of Classification Search
CPC ........... G06K 7/10148; G06K 7/10366; A61M 5/14276; A61M 2205/8243; A61M 2205/04; A61M 2205/3523

See application file for complete search history.

(56) References Cited

U.S. PATENT DOCUMENTS

| | | | |
|---|---|---|---|
| 6,198,971 B1 | 3/2001 | Leysieffer | |
| 2006/0030902 A1 | 2/2006 | Quiles et al. | |
| 2009/0198307 A1 | 8/2009 | Mi et al. | |
| 2009/0228074 A1 | 9/2009 | Edgell et al. | |
| 2011/0087307 A1 | 4/2011 | Carbunaru et al. | |
| 2012/0316540 A1 | 12/2012 | Brennan et al. | |
| 2013/0289334 A1* | 10/2013 | Badstibner | A61M 1/127 600/16 |
| 2013/0310630 A1* | 11/2013 | Smith | A61M 1/127 600/16 |

(Continued)

OTHER PUBLICATIONS

International Search Report and Written Opinion issued in a corresponding International Application No. PCT/US20151043847 dated Nov. 20, 2015.

*Primary Examiner* — Erin M File
(74) *Attorney, Agent, or Firm* — Morgan, Lewis & Bockius LLP (57) ABSTRACT

Systems and methods for maximizing the resonance frequency match between a reader and a controlled device interacting over a narrowband inductive link involve, in various embodiments, features of the controlled device, the reader, or both.

11 Claims, 7 Drawing Sheets

(56) References Cited

U.S. PATENT DOCUMENTS

2016/0045184 A1* 2/2016 Courtney ............ A61B 8/4245
                     600/424

* cited by examiner

IMPLANT TELEMETRY WITH DYNAMIC TUNING

CROSS-REFERENCE TO RELATED APPLICATION

This is a continuation-in-part of U.S. Ser. No. 14/818,510, filed on Aug. 5, 2015, which claims priority to and the benefit of U.S. Provisional Application No. 62/033,557, filed on Aug. 5, 2014. The entire disclosures of the foregoing documents are hereby incorporated by reference.

BACKGROUND

Wireless charging and patient monitoring are becoming increasingly important in medical applications. By incorporating wireless charging technology, medical implants benefit from greater site flexibility, a smaller total footprint and reduced battery size. However, many hurdles still exist for implant devices utilizing inductively based telemetry, including antenna size constraints, the limited number of antennas that may be included in an implant, and the expected attenuation caused by tissue that further weakens the inductive coupling link. All of these factors must be taken into account to achieve reliable patient monitoring, consistent actuation of therapy (e.g., drug delivery, electrical stimulation, etc.) and inductive power transfer for charging the implant battery.

Implantable telemetry applications include pacemakers, medicine delivery pumps, stimulation devices, monitoring systems, and artificial hearts. Implantable drug delivery systems, for example, which may have a refillable drug reservoir, cannula and check valve, etc., allow for controlled delivery of pharmaceutical solutions to a specified target. This approach can minimize the surgical incision needed for implantation and avoids future or repeated invasive surgery or procedures. Refillable ocular drug pumps, for example, usually hold less than 100 μL, are much smaller and more difficult to access post-implantation than other implantable pumps, such as those used for intrathecal injections or insulin therapy.

Thus, an implantable drug-delivery pump may incorporate telemetry to facilitate communication with an external monitoring device and wireless charging of the battery powering the implanted device via inductive coupling. The operating parameters of the implantable pump may be non-invasively adjusted and diagnostic data may be read out from the pump to the external monitoring device through wireless signals. During a scheduled visit, a physician may place the monitoring device near the implantable pump and send wireless signals to the implantable pump. The implant, in turn, adjusts the parameters in the pump and transmits a response command to the monitoring device. Typically, a medical telemetry device comprises a coil antenna that transmits and receives signals using electromagnetic waves. However, other antenna configurations known in the field may be utilized as well. A number of parameters characterizing the efficiency of the coil antenna, e.g., the resonant frequency, gain, quality factor (Q factor), and the thermal effect (Joule effect or heat) are considered when selecting or designing the coil antenna.

The wireless power receiver system may comprise additional electronic components such as a battery, a magnetic core, and circuitry including data storage and a transceiver for data. Some or all of the circuitry is usually hermetically sealed within a device case, but the telemetry coil may be placed externally to mitigate any interference caused by certain case materials. Achieving sufficient power transfer across tissue to an implanted device can pose a major challenge, particularly for small devices.

Figure 1:
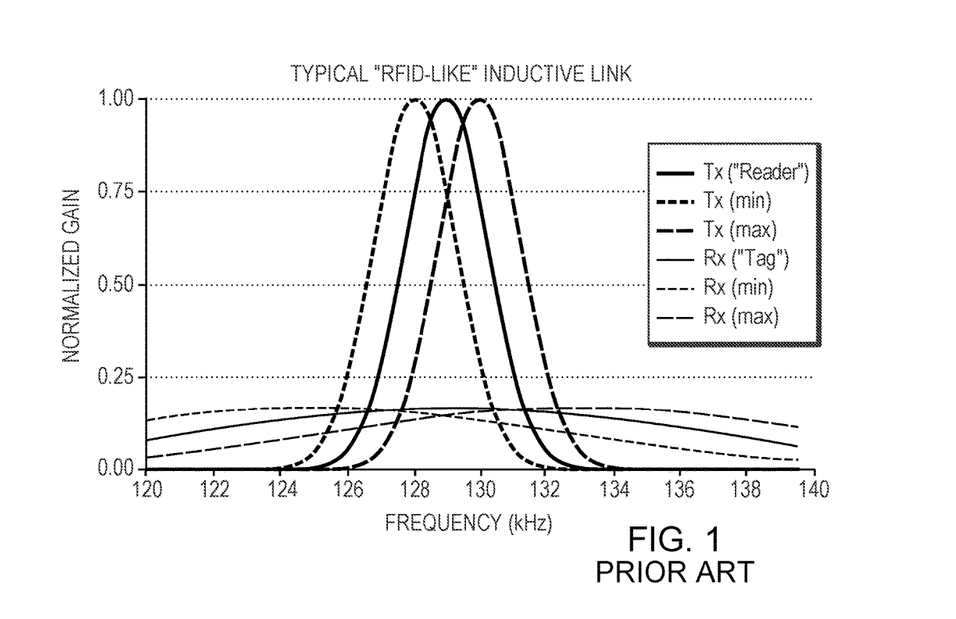
FIGS. 1-4 graphically illustrate the effects of resonance frequency mismatch in broadband and narrowband systems.
Figure 2:
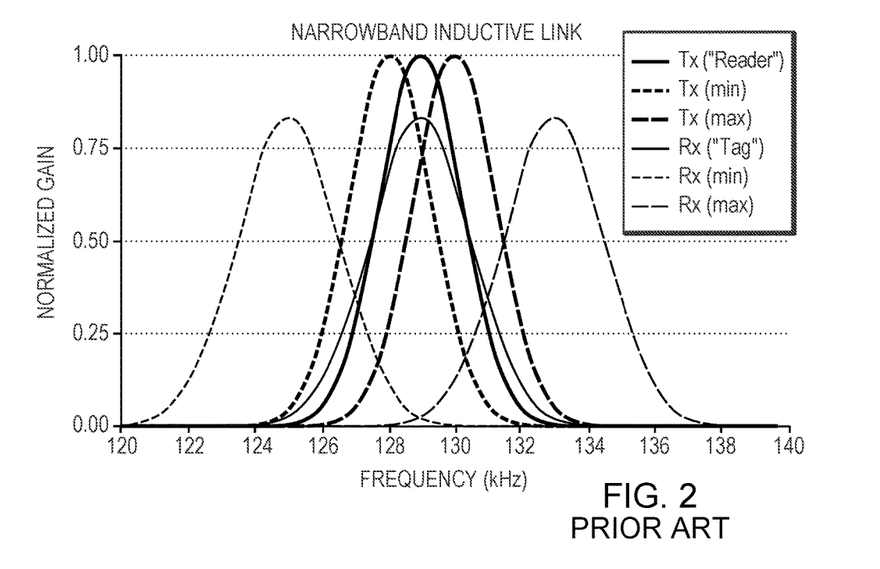

FIGS. 1 and 2 highlight the difference between a small implanted system with telemetry and a traditional system such as a radiofrequency ID (RFID) or similar broadband system, in which a tag or other inductively responsive device is powered and interrogated wirelessly by a reader. As shown in FIG. 1, in a broadband system, the bandwidth of the receiver (i.e., the tag) is sufficiently large for the response to be almost flat across the transmitter bandwidth, even accounting for tolerances; that is, while the degree of inductive coupling is not especially high, it is consistently well above zero across a large frequency band. Consequently, even if the peak transmission frequency varies, it will still transfer power and/or data to the receiver. Comparatively, in a narrowband inductive link such as those employed by small implantable devices, the receiver bandwidth is narrow. Hence, as shown in FIG. 2, it may fail to coincide (or coincide sufficiently) with the transmitter bandwidth, accounting for tolerances, to facilitate adequate power and data transfer. At the same time, when the transmission and frequency bands do coincide, the system achieves much higher normalized gain.

The resonance frequency (in Hertz) of an inductive link is controlled by a capacitor of capacitance C in parallel with the receiving coil of inductance L, and its value is given by the following equation:

$$f_0 = \frac{1}{2\pi\sqrt{LC}}$$

Figure 3:
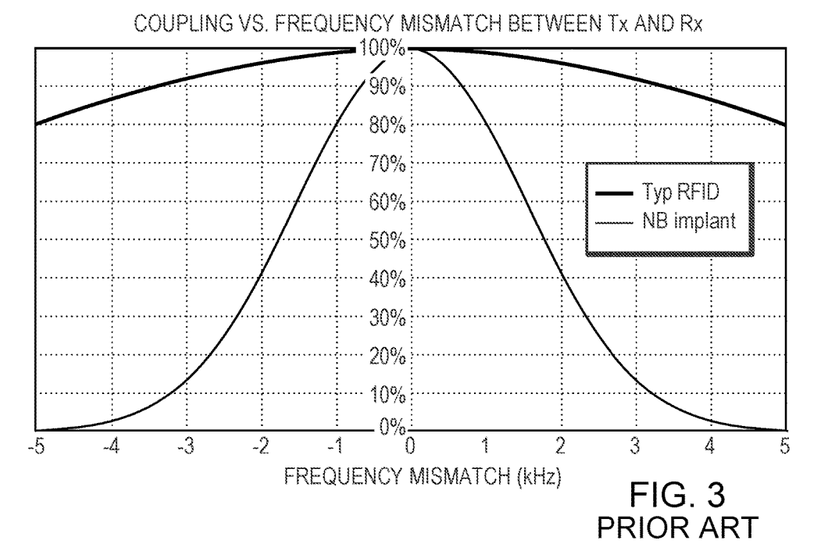
Figure 4:
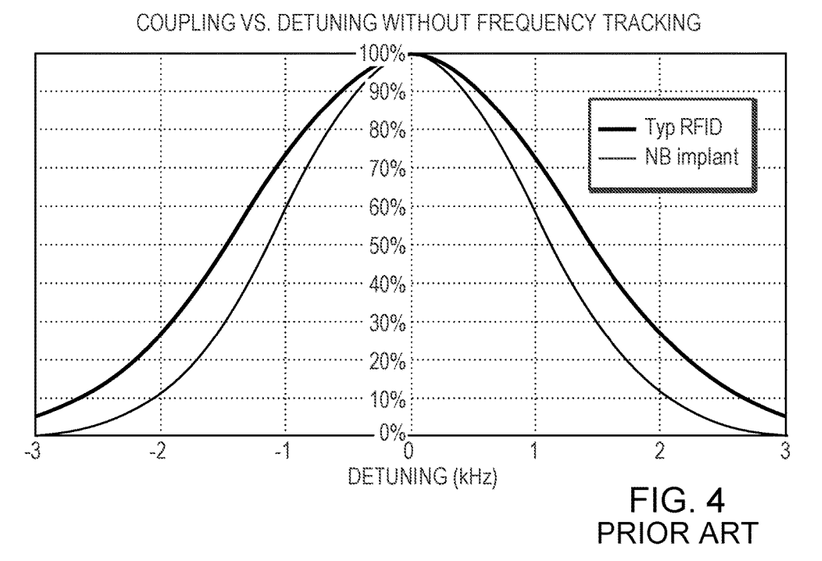

A narrowband system is very sensitive to proper tuning (i.e., the disparity in $f_0$ between receiver and transmitter) and susceptible to any shift of resonance frequency or transmitter frequency drift. The result of a frequency mismatch in broadband and narrowband systems is illustrated in FIG. 3. In a broadband system, the degradation in coupling efficiency remains low across a relatively wide range of frequencies, whereas in a narrowband system, the coupling efficiency drops drastically with even a modest mismatch in resonance frequencies. The faster the drop-off, the more limited will be the practicability of implementing a narrowband system given realistic manufacturing tolerances and inevitable drifts during operation, as illustrated in FIG. 4, which shows the relative effects of detuning or oscillator drift in broadband and narrowband links. As a practical matter, the lower limit of usability is reached when the efficiency falls below 70%, and for the system represented in FIG. 4, this is a frequency mismatch of merely ±1 kHz.

Accordingly, traditional RFID design principles do not readily apply to very small devices utilizing narrowband links. An RFID transmitter is adjusted so that its frequency matches the resonance frequency to obtain maximum power transfer. Oscillator frequency drift or detuning effect is typically dealt with by minimizing its amplitude by design (choice of components, tight tolerance of components) and building the necessary margin into the link budget to cope with the resulting degradation. For a well-designed system, less than 50% degradation can be achieved. In order to maximize the power received for a given receiver coil or minimize the size of the receiver coil for a given power target, the bandwidth of both the transmitter and receiver are narrowed to what is required to still maintain data communication—a few kHz in typical implementations. This ensures the maximum possible combined Q factor and therefore the maximum power transfer. Because the bandwidth of both the transmitter and receiver may only be a few kHz, their resonance frequencies may need to be accurately matched to avoid significant coupling degradation.

SUMMARY

In various embodiments, the present invention relates to strategies for maximizing the resonance frequency match between a reader and a controlled device interacting over a narrowband inductive link. These strategies may involve features of the controlled device, the reader, or both.

The approach described herein is broadly applicable across many implantable, actuated devices, including pacemakers, medicine delivery pumps, stimulation devices, monitoring systems, and artificial hearts.

In an aspect, embodiments of the invention feature an implantable device comprising an electronic actuator; a battery for powering the electronic actuator; control circuitry for controlling operation of the electronic actuator; and a telemetry system, operatively coupled to the battery and to the control circuitry, for (i) wirelessly receiving commands for controlling operation of the electronic actuator over a narrowband inductive link, (ii) wirelessly receiving a power signal for charging the battery over the narrowband inductive link, and (iii) detecting, during a wirelessly transmitted sweep signal, a series of signal amplitudes and reporting at least one of the following: (A) a log of signal amplitudes, (B) an index or time associated with the maximum signal amplitude, or (C) a frequency associated with the maximum signal amplitude. In some embodiments, the telemetry control circuitry is further configured to detect a synchronization signal and, in response thereto, to (i) record a succession of detected signal amplitudes over a sensing period, (ii) generate an in-order log of the detected amplitudes, and (iii) report the log. In other embodiments, the telemetry control circuitry is further configured to detect a synchronization signal and, in response thereto, to (i) record a succession of detected signal amplitudes over a sensing period, (ii) determine an index associated with a maximum one of the recorded signal amplitudes, and (iii) report the index.

The index may be referenced to an internal system time, e.g., so as to specify a time interval between the onset of the sweep signal and detection of the maximum amplitude. Alternatively or in addition, the index may specify the log entry corresponding to the maximum recorded signal amplitude.

In some embodiments, the telemetry control circuitry is further configured to detect a synchronization signal and, in response thereto, to (i) record a succession of detected frequencies and signal amplitudes associated therewith over a sensing period, (ii) determine a frequency corresponding to a maximum one of the signal amplitudes, and (iii) report the frequency. The index and/or frequency may be transmitted over the narrowband link in response to a wirelessly transmitted request therefor, and the telemetry control circuitry may be further configured to receive the resonance frequency of the system over the narrowband link following transmission of the index, and to store the received resonance frequency in the memory.

In another aspect, the invention pertains to a communication system for communicating with an implantable device. In various embodiments, the system comprises a transmitter for transmitting a wireless signal; and an implantable device comprising an electronic actuator; a battery for powering the electronic actuator; control circuitry for controlling operation of the electronic actuator; and a telemetry system, operatively coupled to the battery and to the control circuitry, for wirelessly receiving, from the transmitter over a narrowband inductive link, commands for controlling operation of the electronic actuator and a power signal for charging the battery. The transmitter may be configured to (i) wirelessly transmit a sweep signal to the implantable device, (ii) detect a peak loading during the transmission of the sweep signal, and (iii) transmit the commands and the power signal over a frequency corresponding to the detected peak loading. In some embodiments, the transmitter comprises phase-locked loop circuitry for maintaining transmission at the resonance frequency.

In yet another aspect, the invention relates to a reader for wirelessly communicating with an implanted device over a narrowband inductive link. In various embodiments, the reader comprises a resonator circuit; and control circuitry for (i) operating the resonator circuit to wirelessly transmit a sweep signal to the implantable device, (ii) detecting a peak loading during the transmission of the sweep signal, and (iii) transmitting the commands and the power signal over a frequency corresponding to the detected peak loading. In some embodiments, the reader further comprises phase-locked loop circuitry for maintaining transmission at the resonance frequency. For example, the phase-locked loop circuitry may comprise or consist of an amplifier, a tuning circuit, an amplitude detector, comparator, and a filter.

In other embodiments, the reader comprises resonator circuitry for transmitting the commands and the power signal over the narrowband inductive link at a resonance frequency; and phase-locked loop circuitry for maintaining transmission at the resonance frequency. In such embodiments, the reader may further comprises control circuitry configured to determine the resonance frequency of the implanted device by wireless interaction therewith. For example, the control circuitry may be configured to determine the resonance frequency of the implanted device by (i) transmitting a wireless signal whose frequency varies over time and (ii) detecting, during the transmission, a peak loading whose frequency corresponds to the resonance frequency. Alternatively, the control circuitry may be configured to determine the resonance frequency of the implanted device by (i) transmitting a wireless signal whose frequency varies over time, (ii) receiving, from the implanted device, either a log of entries each having an amplitude and/or the index of the maximum recorded amplitude, and (iii) based on the log, determining the frequency corresponding to a peak amplitude. In some embodiments, the log is time-indexed, and the resonance frequency is determined by matching the log entry corresponding to the largest amplitude with a corresponding frequency of the wireless signal.

The term "substantially" or "approximately" means ±10% (e.g., by weight or by volume), and in some embodiments, ±5%. The term "consists essentially of" means excluding other materials that contribute to function, unless otherwise defined herein. Nonetheless, such other materials may be present, collectively or individually, in trace amounts. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

The foregoing will be more readily understood from the following detailed description of the invention, in particular, when taken in conjunction with the drawings, in which.

DETAILED DESCRIPTION

Figure 5:
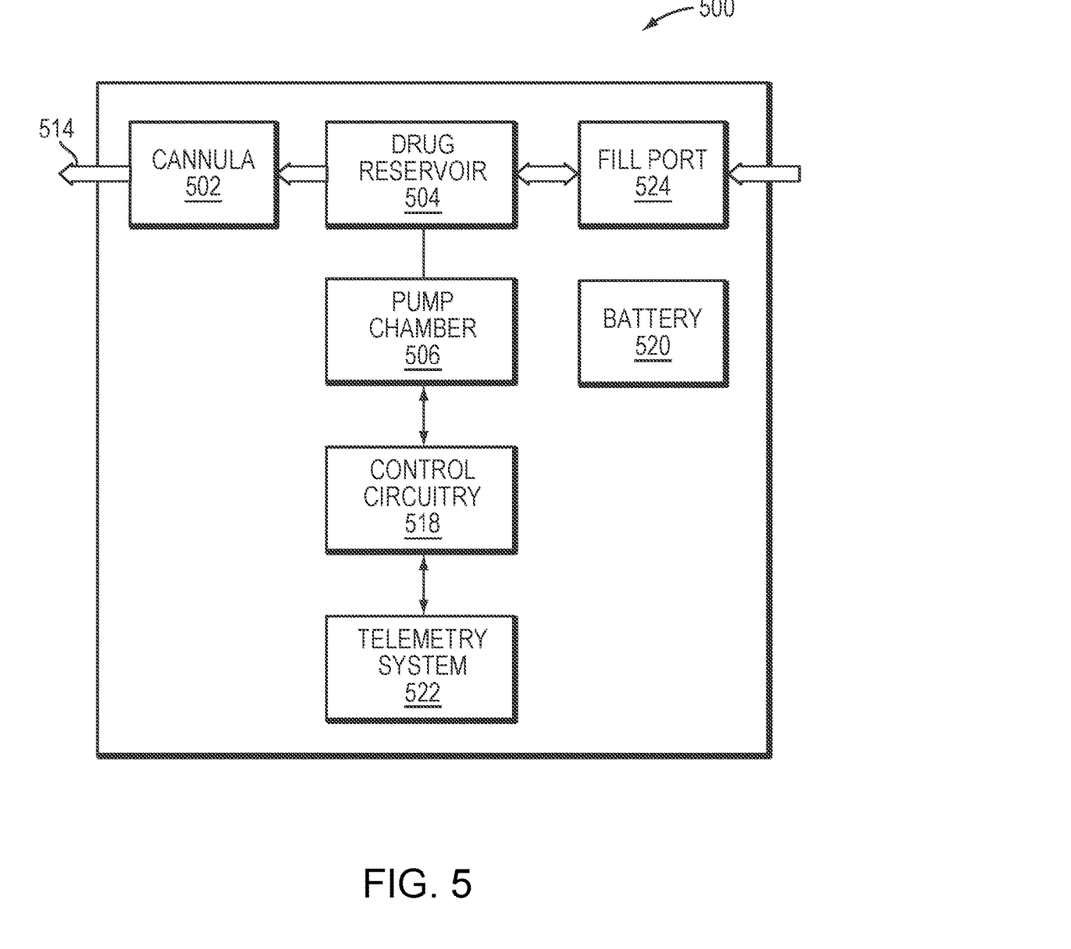
FIG. 5 is a block diagram of an implantable device incorporating an embodiment of the invention.

A representative environment for a telemetry application in accordance herewith is an implantable drug-delivery pump as illustrated in FIG. 5. The drug pump device 500 includes a cannula 502 and a pair of chambers 504, 506. The top chamber 504 defines a drug reservoir that contains the drug to be administered in liquid form, and the bottom chamber 506 contains a liquid which, when subjected to electrolysis using electrolysis electrodes, evolves a gaseous product. The two chambers are separated by a corrugated diaphragm (not shown). The cannula 502 connects the top drug chamber 504 with a check valve 514 inserted at the site of administration. Control circuitry 518, a battery 520, and a telemetry system 522 for power and data transmission are embedded within the device 500. Depending on the complexity of the control functionality it provides, the control circuitry 518 may be implemented, e.g., in the form of analog circuits, digital integrated circuits (such as, e.g., microcontrollers), or programmable logic devices, and the telemetry system 522 may be integrated in whole or in part within the control circuitry 518. In some embodiments, the control circuitry 518 includes a microprocessor and associated memory for implementing complex drug-delivery protocols. The drug pump device 500 may also include various sensors (e.g., pressure and flow sensors) for monitoring the status and operation of the various device components, and such data may be logged in the memory for subsequent retrieval and review. For the prolonged use of the drug pump device 500 following implantation, the device includes one or more fill ports 524 in fluid communication with the drug reservoir 504, which permit a refill needle (not shown) to be inserted therethrough. Additional features of implantable drug-delivery pumps usable in accordance with embodiments of the present invention may be found in U.S. Pat. No. 8,231,608, filed on May 8, 2009, the entire disclosure of which is incorporated by reference herein.

Figure 6:
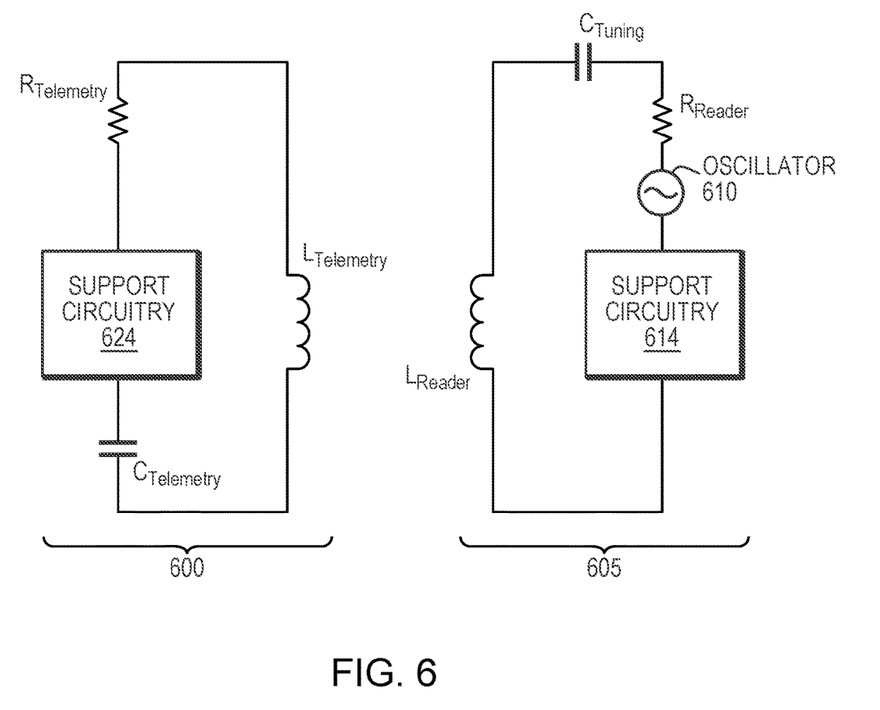
FIG. 6 schematically illustrates a reader and an inductively linked telemetry system in accordance with embodiments of the invention.

With reference to FIG. 6, a representative telemetry system (or "receiver") 600 communicates inductively with a reader (or "transmitter") 605 over a narrowband link. The reader 605 includes a tuning circuit (which includes or consists essentially of, for example, a capacitance (e.g., one or more capacitors) $C_{Tuning}$ and an inductance (e.g., one or more inductors) $L_{Reader}$), an AC signal source (or "oscillator") 610, and support (or "control") circuitry 614 that may include an optional memory that may include volatile and/or non-volatile components. The internal resistance (and additional impedance) of the reader 605 is represented as a resistance $R_{Reader}$. The inductor $L_{Reader}$ may serve as the system antenna, or the reader 605 may utilize a separate antenna. The telemetry system 600 includes a capacitance (e.g., one or more capacitors) $C_{Telemetry}$, an inductance (e.g., one or more inductors) $L_{Telemetry}$, and support circuitry 624 that may include or consist essentially of, e.g., a microcontroller or microprocessor and a computer memory having volatile and nonvolatile components. The internal resistance (and additional impedance) of the telemetry system 600 is represented as a resistance $R_{Telemetry}$. As noted earlier, these components may be discrete or may be within the control circuitry 518 described above. In operation, $C_{Tuning}$ and $L_{Reader}$ form a resonator (or "resonator circuit") driven by the AC source 610. When inductively coupled to the telemetry system 600 via the inductor $L_{Telemetry}$, the signal produced by the AC source supplies power and/or a data signal to the telemetry system 600, charging the battery 520 and operating or communicating with the control circuitry 518 (see FIG. 5). Because the inductive link is narrowband, it is important for resonance frequencies of the systems 600, 605 to match as closely as practicable, and for the AC source 610 to operate at substantially this frequency. Data signals may be transmitted to the telemetry system 600 by amplitude modulation of the time-varying AC signal (where the AC frequency is fixed and data is encoded in an amplitude-modulated signal envelope) or frequency modulation of the signal (where the AC frequency is varied in accordance with the transmitted data, but does not deviate significantly from the resonance frequency).

In practice, both L and C components have manufacturing tolerances that typically preclude a precise match of the resonance frequencies. This difference or shift may be tolerable as long as the effective resonance frequency remains within the frequency band allowed by regulation (i.e., 119 kHz to 135 kHz or other allowable medical frequency band). Selecting a tuning capacitor with a rated ±1% tolerance provides a tolerance budget for the coil inductance (which is more difficult to control) of up to ±10%. Typically, however, tighter control of the resonance frequency is necessary or desirable to avoid excessive attenuation in a narrowband link. In one approach, the support circuitry 624 contains a plurality of capacitors that may each be selectively activated or deactivated. For example, the capacitors may be arranged in parallel with fusible links. During system testing following manufacture, selected ones of the capacitors are deactivated by, for example, laser exposure or localized application of a voltage pulse, and the final capacitance of the sum of the capacitances of the capacitors that have not been deactivated. Alternatively, each capacitor may be connected a transistor (e.g., a MOSFET) configured as a switch, and which is operated by the support circuitry 624 (e.g., by a microcontroller therewithin). During final testing, the proper capacitance (i.e., the capacitance at which the correct resonance frequency is attained) is determined and a binary "image" of the switch states corresponding this capacitance is permanently stored in the memory of the support circuitry 624 as the pedigree of the device; when the device is powered on, this value is loaded and the transistors are operated accordingly.

This approach may not be practical for a very small device because of the space required for multiple capacitors and their switches. For such a device, an advantageous approach is to minimize the number of components in the device itself, design their tolerances such that the resonance frequency is always within the allowed band and push the frequency-tracking complexity to the reader 605, which has fewer size constraints. Again, because of the narrowband link, the bandwidth is typically limited to only a few kHz to maximize the Q factor and thereby permit sufficient power transfer, and the resonance frequencies of the reader 605 and the telemetry system 600 should be accurately matched.

Thus, in an alternative embodiment, the multiple capacitors are disposed within the support circuitry 614 of the transmitter 605 rather than in the receiver 600. To keep the receiver small, no adjustment is made to its resonance frequency; the component tolerances are specified such that the resonance frequency will always fall within an acceptable frequency range. The transmitter 605 is tuned—e.g., the total capacitance is varied—until a matching frequency is achieved. In this way, a single reader 605 can be used with many receivers 600, and can store, in non-volatile memory of the support circuitry 614, a table of receiver identifiers each associated with the determined capacitance (or resonance frequency) for that receiver. When a new receiver session begins, the reader 605 interrogates the receiver 600, obtains its identifier, and if it locates the identifier in its stored look-up table, it activates the proper number of capacitors to achieve the stored value. If the identifier is not found, the transmitter 605 is tuned.

Figure 7:
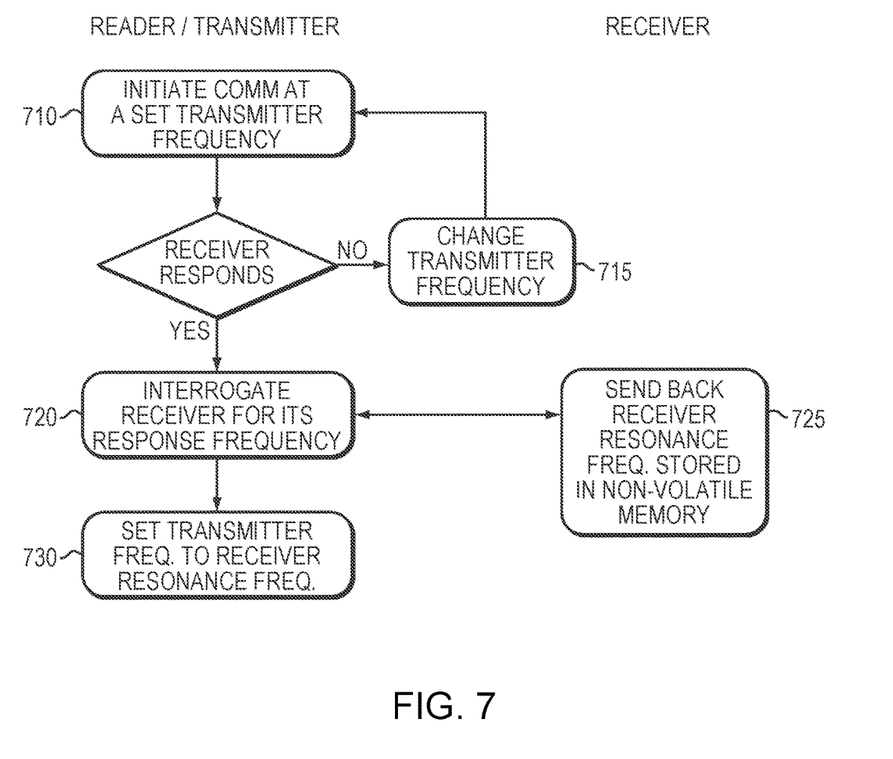
FIG. 7 is a workflow diagram illustrating a procedure for establishing the resonance frequency of a telemetry receiver in accordance with embodiments of the invention.

An embodiment of a tuning process, performed to discover the resonance frequency of the receiver and store its value for future use, is illustrated in FIG. 7. Some or all of the steps may occur during the manufacturing process (e.g., prior to implant of the device within a patient). In a first step 710, the transmitter initiates communication with the receiver at an expected resonance frequency. This frequency may not be optimal in terms of power transfer, but will typically be sufficiently close to permit communication under static conditions. If the receiver does not respond, however, the transmitter frequency is altered (step 715) by the support circuitry 614 (see FIG. 6), and steps 710 and 715 repeat until communication is established. At this point (step 720), the transmitter interrogates the receiver to determine whether the latter can transmit a resonance frequency that has been determined and/or set during manufacture. If so (step 725), the transmitter receives the frequency and sets its internal oscillation frequency accordingly (step 730). Alternatively or in addition, the receiver may obtain an identifier from the receiver. If the transmitter receives both an identifier and a resonance frequency, it may save the tuple as a database record in nonvolatile storage. If the receiver provides no resonance frequency, it may still provide an identifier, such as a serial number. For medical devices, this is documented as part of the device master record and subsequently transferred to the patient record in the case of an implant. This allows for easy access in the future from the cloud or other server system.

It should be understood that wireless communication and reporting of data (such as the resonance frequency) can occur actively or passively. In an active system, communication is bidirectional and the receiver transmits data to the transmitter over the wireless link. In a passive system, the receiver modulates the received signal in accordance with the data to be transferred; this modulation is detected and interpreted by the transmitter. For example, the receiver may modulate the power transfer by selectively switching, in a pattern corresponding to data, a resistance into the LC resonator.

Figure 8:
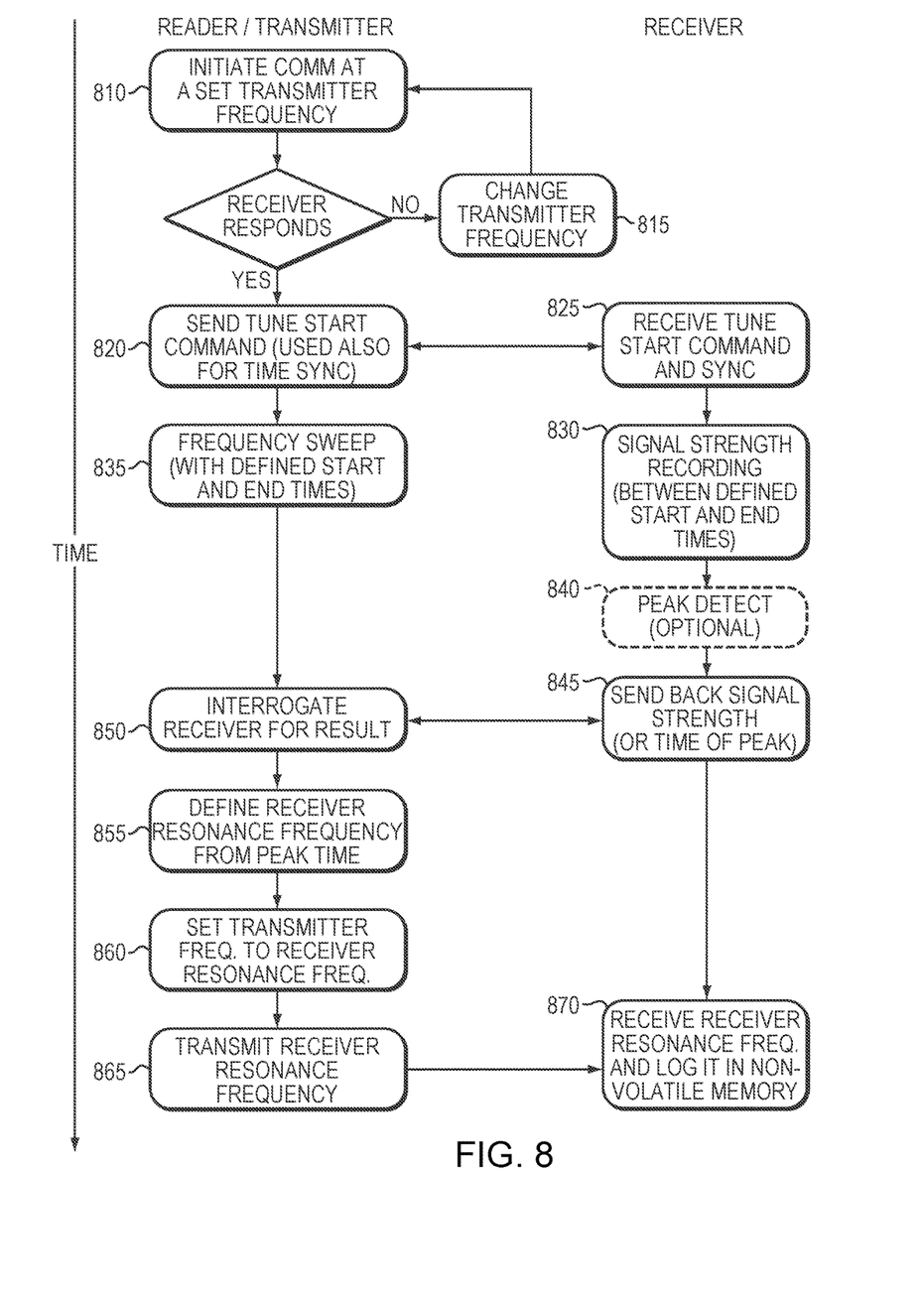
FIG. 8 is a workflow diagram illustrating a procedure for establishing the resonance frequency of a telemetry receiver for the first time.

If the receiver has not stored its resonance frequency, the procedure illustrated in FIG. 8 may be undertaken. In steps 810, 815, the transmitter varies its oscillation frequency until communication with the receiver is established. To facilitate tuning, the transmitter and receiver establish synchronization. This begins with a "tune start" command sent by the transmitter (step 820), which is received (step 825) and causes the receiver to begin recording the signal strengths of communications received from the transmitter (step 830). The transmitter sends signals that sweep through a band of frequencies around the expected resonance frequency (step 835); for example, the frequency band may reflect the maximum expected frequency variation given manufacturing tolerance limits. The amplitudes of these signals are sensed and/or recorded by the receiver. In some embodiments, the receiver is configured to detect the peak signal strength (step 840) without necessarily recording an absolute amplitude level, and to transmit the corresponding frequency back to the transmitter (step 845) when interrogated for the result by the transmitter (step 850). In other embodiments, the receiver simply records a log of signal strengths (and, in some embodiments, corresponding sensed frequencies), and sends the log back in response to the interrogation signal; in this case, the transmitter is programmed to examine the log and identify the frequency with the peak signal strength (i.e., the largest log entry). In addition to signal strengths (i.e., amplitudes), log entries may store frequency values, as suggested above, or may instead store indices that correspond to those values. This approach limits the amount data stored on receiver. For example, the indices may be simple ascending integers each corresponding to a time interval or may otherwise correspond to elapsed times during the frequency sweep (i.e., the log may be time-indexed). Alternatively, the indices may be hashed values based on the time, the frequency and/or other relevant parameters, and which the transmitter may use to reconstruct or retrieve the parameters. In this way, the transmitter may access multiple relevant parameters without necessitating their storage on the receiver.

For example, the receiver may record a sequence of absolute times and the amplitude of the received signal at each such time. Alternatively, the receiver may record the amplitude at fixed intervals beginning with the tune start command, e.g., as a series of paired values (sample number and amplitude) in a log. Upon interrogation, the receiver reports either the full log of entries (each having an amplitude) or the log index associated with the maximum amplitude. The index may be "system-referenced" (e.g., reference an internal clock (typically the MCU clock) so that the samples originate at a specific system-determined time and the log indices specify successive time intervals thereafter). Because the sampling interval is fixed, this functions as a timestamp. The transmitter computes the time elapsed between the tune start command and the reported sample number of the peak amplitude, and determines, based on the sweep rate, which frequency during the sweep was active at the elapsed time. Thus, either the absolute time or the sample number of the peak amplitude (or a hash based in whole or in part on either) can function as a timestamp provided to the transmitter upon interrogation.

The transmitter selects this frequency as its oscillation (transmission) frequency (steps 855, 860) and uses this frequency during its communication session with the receiver. In some embodiments, the transmitter also sends data identifying this frequency to the receiver (step 865), which records it (step 870) for subsequent transmission upon interrogation (FIG. 7, step 725) so that the procedure of FIG. 7 can subsequently be used. Alternatively or in addition, the transmitter may associate the retrieved serial number with the discovered resonance frequency in a database record.

In various embodiments of the invention, the transmitter determines the resonance frequency without receiving a pre-set, stored resonance frequency or the above-described log from the receiver. In such embodiments, the transmitter may send signals that sweep through a band of frequencies around the expected resonance frequency, as described for step 835 above. During the frequency sweep, signal strengths are not detected or stored by the receiver. Instead, the transmitter determines the resonance frequency by determining the frequency during the sweep when the transmitter loading (i.e., the power transferred by the transmitter over the resonant link with the receiver) is maximized. The maximum loading may be detected and the corresponding frequency identified by any suitable method, e.g., repeated comparisons during the sweep of a current loading level to a previously determined maximum. Whether the resonance frequency is discovered by the receiver or the transmitter, only a single frequency sweep is ordinarily necessary.

Figure 9:
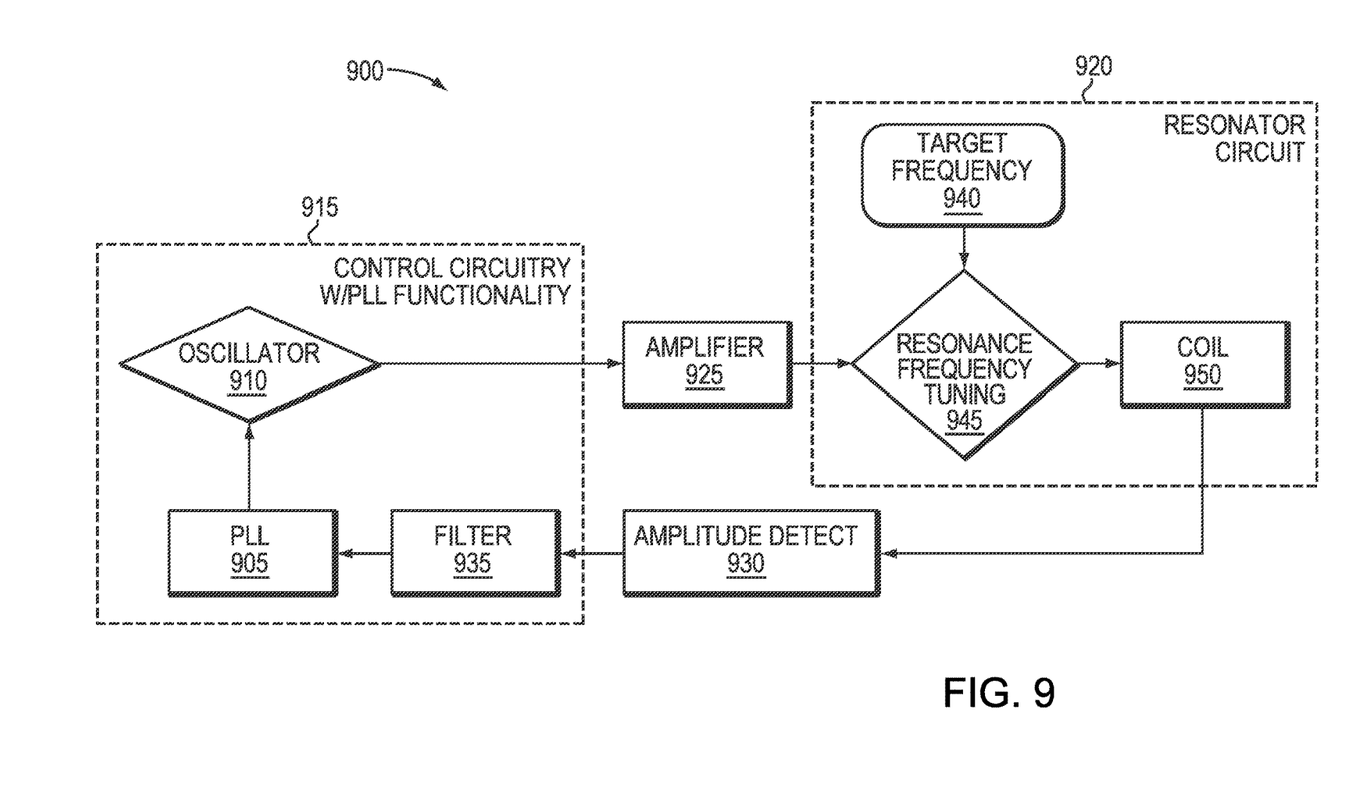
FIG. 9 schematically illustrates a functional flow chart of a phase-locked loop configuration in accordance with embodiments of the invention.

FIG. 9 illustrates the components and functional flow of a circuit 900 using a conventional phase-locked loop (PLL) 905 in the transmitter design to maintain the oscillator at the resonant frequency. Here, the carrier frequency of the transmitter is not set by the oscillator 910 as in a traditional implementation, but instead the oscillator 910 tracks the resonance frequency of the transmitter 605. The circuit 900, which may be included within the support circuitry 614 of the transmitter (see FIG. 6), includes a control circuit block 915, a resonator circuit block 920, an amplifier 925, and an amplitude detector 930. As shown, the control circuit block 915 may include the PLL 905, the oscillator 910, and a low-pass filter 935. The illustrated loop configuration maintains a target frequency 940, i.e., the transmitter's resonance frequency, obtained from the receiver during setup or determined as described above. A tuning circuit (or "tuning block") 945 in the resonator circuit block 920 may operate in the manner described above, selectively switching in capacitors arranged in parallel to achieve and maintain the target frequency; or by adjusting the inductance—e.g., by selectively advancing a magnetically permeable core into the interior of a coil 950. The further the core is advanced into the coil (e.g., by a stepper motor), the greater will be the inductance. An advantage to adjusting the inductance in this way is that the adjustment may be continuous or essentially so, as contrasted with the step adjustment to capacitance. The PLL adjusts the oscillator frequency such that the amplitude of oscillation at the coil is maximized, i.e., matching the resonance frequency. The detector 930 measures the amplitude of oscillation by, for example, extracting it using an envelope detector followed by filtering by the filter 935 to remove any noise and modulation.

It should be emphasized that the control and support circuitry described above may be implemented in hardware, software or a combination of the two. For embodiments in which the functions are provided as one or more software programs, the programs may be written in any of a number of high level languages such as FORTRAN, PYTHON, JAVA, C, C++, C#, BASIC, various scripting languages, and/or HTML. Additionally, the software can be implemented in an assembly language directed to the microprocessor; for example, the software may be implemented in Intel 80x86 assembly language if it is configured to run on an IBM PC or PC clone. The software may be embodied on an article of manufacture including, but not limited to, a floppy disk, a jump drive, a hard disk, an optical disk, a magnetic tape, a PROM, an EPROM, EEPROM, field-programmable gate array, or CD-ROM. Embodiments using hardware circuitry may be implemented using, for example, one or more FPGA, CPLD or ASIC processors.

Various embodiments of the invention are described above. It will, however, be apparent to those of ordinary skill in the art that other embodiments incorporating the concepts disclosed herein may be used without departing from the spirit and scope of the invention. Accordingly, the above description is intended to be only illustrative and not restrictive.

What is claimed is:

1. An implantable device comprising:
an electronic actuator;
a battery for powering the electronic actuator;
control circuitry for controlling operation of the electronic actuator; and
a telemetry system, operatively coupled to the battery and to the control circuitry, for (i) wirelessly receiving commands for controlling operation of the electronic actuator over a narrowband inductive link, (ii) wirelessly receiving a power signal for charging the battery over the narrowband inductive link, and (iii) detecting, during a wirelessly transmitted sweep signal, a series of signal amplitudes and reporting at least one of (A) a log of signal amplitudes, (B) an index or time associated with the maximum signal amplitude, or (C) a frequency associated with the maximum signal amplitude.

2. The device of claim 1, wherein the telemetry system is further configured to detect a synchronization signal and, in response thereto, to (i) record a succession of detected signal amplitudes over a sensing period, (ii) generate an in-order log of the detected amplitudes, and (iii) report the log.

3. The device of claim 1, wherein the telemetry system is further configured to detect a synchronization signal and, in response thereto, to (i) record a succession of detected signal amplitudes over a sensing period, (ii) determine an index associated with a maximum one of the recorded signal amplitudes, and (iii) report the index.

4. The device of claim 3, wherein the index is referenced to an internal system time and thereby specifies a time interval between onset of the sweep signal and detection of the maximum amplitude.

5. The device of claim 3, wherein the index specifies the log entry corresponding to the maximum recorded signal amplitude.

6. The device of claim 1, wherein the telemetry system is further configured to detect a synchronization signal and, in response thereto, to (i) record a succession of detected frequencies and signal amplitudes associated therewith over a sensing period, (ii) determine a frequency corresponding to a maximum one of the signal amplitudes, and (iii) report the frequency.

7. The device of claim 3, wherein the index is transmitted over the narrowband link in response to a wirelessly transmitted request therefor.

8. The device of claim 7, wherein the telemetry system is further configured to receive the resonance frequency of the system over the narrowband link following transmission of the index, and to store the received resonance frequency in the memory.

9. The device of claim 6, wherein the frequency is transmitted over the narrowband link in response to a wirelessly transmitted request therefor.

10. A communication system for communicating with an implantable device, the system comprising:
- a transmitter for transmitting a wireless signal; and
- an implantable device comprising:
- an electronic actuator;
- a battery for powering the electronic actuator;
- control circuitry for controlling operation of the electronic actuator; and
- a telemetry system, operatively coupled to the battery and to the control circuitry, for wirelessly receiving, from the transmitter over a narrowband inductive link, commands for controlling operation of the electronic actuator and a power signal for charging the battery,
- wherein the transmitter is configured to (i) wirelessly transmit a sweep signal to the implantable device, (ii) detect a peak loading during the transmission of the sweep signal, and (iii) transmit the commands and the power signal over a frequency corresponding to the detected peak loading.

11. The system of claim 10, wherein the transmitter comprises phase-locked loop circuitry for maintaining transmission at the resonance frequency.

* * * * *